US00PP13400P2

(12) United States Plant Patent
Dümmen

(10) Patent No.: US PP13,400 P2
(45) Date of Patent: Dec. 24, 2002

(54) POINSETTIA PLANT NAMED 'DUESPOTMAR'

(75) Inventor: Marga Dümmen, Rheinberg (DE)

(73) Assignee: Dümmen Jungpflanzenkulturen, Rheinberg (DE)

( * ) Notice: Subject to any disclaimer, the term of this patent is extended or adjusted under 35 U.S.C. 154(b) by 0 days.

(21) Appl. No.: 09/996,371

(22) Filed: Nov. 30, 2001

(51) Int. Cl.[7] ..... A01H 5/00

(52) U.S. Cl. ..... Plt./303

(58) Field of Search ..... Plt./303, 304

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Poinsettia plant named 'Duespotmar', characterized by its inflorescences with pink and pale yellow bi-colored flower bracts; dark green-colored leaves with green-colored petioles; uniform and rounded plant habit; and excellent post-production longevity.

1 Drawing Sheet

BOTANICAL CLASSIFICATION/CULTIVAR DENOMINATION

*Euphorbia pulcherrima* Willd. cultivar Duespotmar.

BACKGROUND OF THE INVENTION

The present Invention relates to a new and distinct cultivar of Poinsettia plant, botanically known as *Euphorbia pulcherrima* Willd., and hereinafter referred to by the name 'Duespotmar'.

The new Poinsettia is a product of a planned breeding program conducted by the Inventor in Rheinberg, Germany. The objective of the breeding program is to create new Poinsettia cultivars with uniform plant habit and attractive flower bract coloration.

The new Poinsettia is a naturally-occurring whole plant mutation of the *Euphorbia pulcherrima* Willd. cultivar HWD Spotlight, disclosed in U.S. Plant Pat. No. 9,854. The new Poinsettia was discovered and selected by the Inventor as a single plant within a population of plants of the cultivar HWD Spotlight in a controlled environment in Rheinberg, Germany. The selection of this plant was based on its attractive flower bract coloration and uniform plant habit.

Asexual reproduction of the new Poinsettia by vegetative terminal cuttings taken at Rheinberg, Germany, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Duespotmar'. These characteristics in combination distinguish 'Duespotmar' as a new and distinct cultivar:

1. Inflorescences with pink and pale yellow bi-colored flower bracts.

2. Dark green-colored leaves with green-colored petioles.

3. Uniform and rounded plant habit.

4. Excellent post-production longevity.

Compared to plants of the parent, the cultivar HWD Spotlight, plants of the new Poinsettia have darker green leaves, longer flower bract petioles, and fewer cyathia per corymb. In addition, plants of the new Poinsettia and the cultivar HWD Spotlight differ in flower bract coloration as plants of the cultivar HWD Spotlight have red-colored flower bracts.

Plants of the new Poinsettia can be compared to plants of the cultivar Marblestar, disclosed in U.S. Plant Pat. No. 9,685. In side-by-side comparisons conducted in Rheinberg, Germany, plants of the new Poinsettia differed from plants of the cultivar Marblestar in the following characteristics:

1. Plants of the new Poinsettia were slightly shorter than plants of the cultivar Marblestar.

2. Plants of the new Poinsettia were more freely branching than plants of the cultivar Marblestar.

3. Plants of the new Poinsettia had smaller and darker green leaves than plants of the cultivar Marblestar.

4. Plants of the new Poinsettia had smaller flower bracts than plants of the cultivar Marblestar.

5. Plants of the new Poinsettia and the cultivar Marblestar differed in flower bract coloration as plants of the cultivar Marblestar had light red and light pink bi-colored flower bracts.

BRIEF DESCRIPTION OF THE PHOTOGRAPH

The accompanying colored photograph illustrates the overall appearance of the new Poinsettia, showing the colors as true as it is reasonably possible to obtain in colored reproductions of this type. Colors in the photograph may differ slightly from the color values cited in the detailed botanical description which accurately describe the colors of the new Poinsettia. The photograph comprises a side perspective view of a single flowering plant of 'Duespotmar' grown in a container.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype.

The aforementioned photographs, following observations and averaged measurements describe plants grown in Rheinberg, Germany during the winter under commercial practice in a glass-covered greenhouse with day and night temperatures about 22° C. and light levels about 4,500 foot-candles. Single plants were grown in 14-cm pots and pinched once. Plants were flowered under natural season short day/long night conditions. Plants were about 17 weeks from unrooted cuttings when the photographs and the detailed botanical description were taken.

In the following description, color references are made to The Royal Horticultural Society Colour Chart, 1995 edition, except where general terms of ordinary dictionary significance are used.

Botanical classification: *Euphorbia pulcherrima* Willd. cultivar Duespotmar.

Parentage: Naturally-occurring whole plant mutation of the *Euphorbia pulcherrima* Willd. cultivar HWD Spotlight, disclosed in U.S. Plant Pat. No. 9,854.

Propagation:

*Type cutting.*—Vegetative terminal cuttings.

*Time to initiate roots.*—Summer: About 9 days at 22° C. Winter: About 13 days at 22° C.

*Time to develop roots.*—Summer: About 21 days at 22° C. Winter: About 28 days at 22° C.

*Root description.*—Thick, fibrous and freely-branching.

Plant description:

*Plant form.*—Inverted triangle, top of plant rounded.

*Growth habit.*—Upright and uniform plant habit.

*Plant height.*—About 21.5 cm.

*Plant diameter or spread.*—About 45 cm.

*Lateral branch description.*—Quantity per plant: About seven to eight lateral branches develop after pinching. Length: About 13.5 cm. Diameter: Less than 1 cm. Internode length: About 1.1 cm. Color: 137C.

*Foliage description.*—Arrangement: Alternate, single. Quantity of leaves per lateral branch: About nine. Length: About 7 cm. Width: About 5 cm. Shape: Mostly ovate with irregular lobing. Apex: Acuminate to apiculate. Base: Obtuse. Margin: Entire with irregular lobing. Venation pattern: Pinnate. Texture, upper and lower surfaces: Glabrous. Surface: Rugose. Color: Young foliage, upper surface: 137A. Young foliage, lower surface: 137C. Fully expanded foliage, upper surface: 131A. Fully expanded foliage, lower surface: 137B. Venation, upper and lower surfaces: 138C. Petiole: Length: About 8.25 cm. Diameter: About 2.5 mm. Texture: Glabrous. Color, upper and lower surfaces: 144D.

Inflorescence description:

*Inflorescence type and habit.*—Inflorescences are compound corymbs of cyathia with colored flower bracts subtending the cyathia. Inflorescences are not fragrant. Inflorescences persistent.

*Natural flowering season.*—Autumn/winter in Northern Hemisphere. Flower initiation and development is induced under long nyctoperiod conditions. Response time, about nine weeks.

*Post-production longevity.*—Plants of the new Poinsettia maintain good substance and bract color for about eight weeks under interior conditions and about 12 to 14 weeks under greenhouse conditions.

*Quantity of inflorescences per plant.*—One per lateral branch, about seven to eight.

*Inflorescence size.*—Diameter: About 19 cm. Height (depth): About 2.75 cm.

*Flower bracts.*—Quantity of flower bracts per inflorescence: About eleven. Length, largest bracts: About 6.9 cm. Width, largest bracts: About 5.2 cm. Shape: Mostly ovate with irregular lobing. Apex: Acuminate to apiculate. Base: Obtuse. Margin: Entire with irregular lobing. Texture, upper and lower surfaces: Glabrous, velvety. Surface: Rugose. Orientation: Mostly horizontal. Color: Developing bracts, upper and lower surfaces: Center, 51B, surrounded by 4D to margin. Fully developed bracts, upper and lower surfaces: Center, 51C, surrounded by 1D to margin; colors fading to 51D surrounded by 2D with subsequent development. Venation, upper and lower surfaces: Same as lamina. Bract petiole: Length: About 4.5 cm. Diameter: About 2 mm. Texture: Glabrous. Color: 144D.

*Cyathia.*—Quantity of cyathia per corymb: About eleven. Diameter of cyathia cluster: About 3 cm. Length: About 6 mm. Diameter: About 4 mm. Shape: Ovoid. Color: Immature: 144A. Mature: 144B. Peduncle: Length: About 3 mm. Diameter: Less than 1 mm. Strength/aspect: Moderately strong, curved. Color: 144B. Stamens: Quantity of stamens per cyathium: About seven. Anther shape: Oval. Anther length: About 1 mm. Anther color: 6B. Amount of pollen: Scarce. Pollen color: 14A. Pistils: Quantity of pistils per cyathium: One. Pistil length: About 9 mm. Style length: About 2 mm. Style color: 145D. Stigma color: 8A. Nectaries: Quantity of nectaries per cyathium: One. Color: 12A.

Disease/pest resistance: Resistance to pathogens and pests common to Poinsettias has not been observed on plants grown under commercial conditions.

It is claimed:

1. A new and distinct cultivar of Poinsettia plant named 'Duespotmar', as illustrated and described.

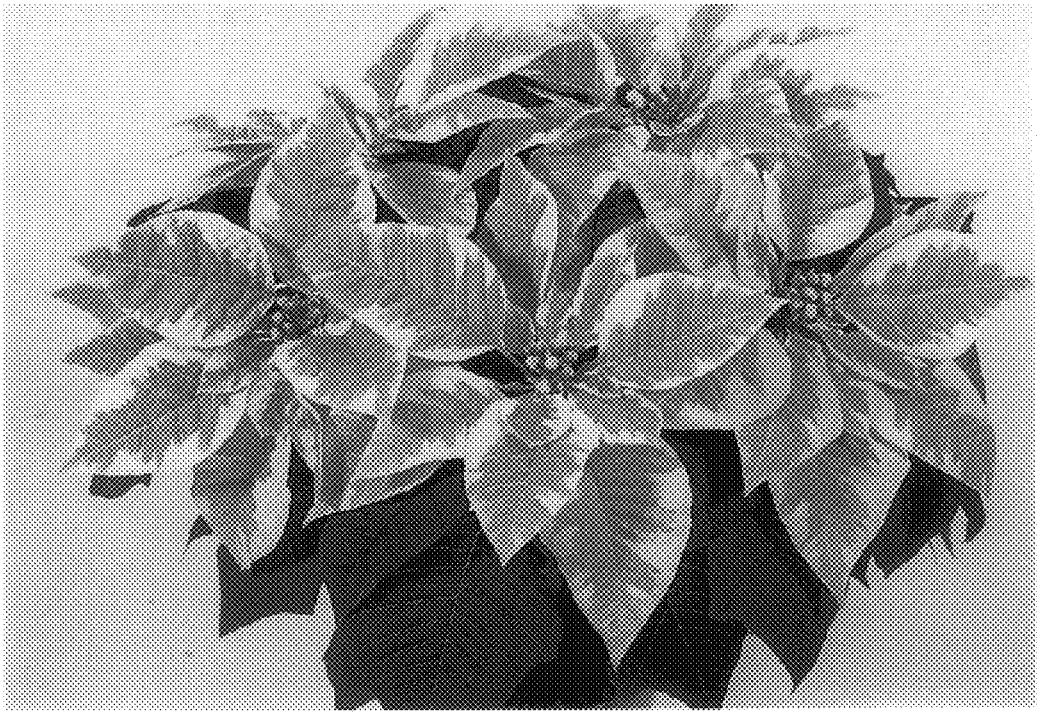

* * * * *